US012376943B2

(12) United States Patent
Li et al.

(10) Patent No.: US 12,376,943 B2
(45) Date of Patent: Aug. 5, 2025

(54) METHODS AND SYSTEMS FOR FORMING A THREE-DIMENSIONAL MODEL OF DENTITION

(71) Applicant: Align Technology, Inc., San Jose, CA (US)

(72) Inventors: Guotu Li, Apex, NC (US); Christopher E. Cramer, Durham, NC (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 18/340,025

(22) Filed: Jun. 22, 2023

(65) Prior Publication Data
US 2024/0024075 A1    Jan. 25, 2024

Related U.S. Application Data

(63) Continuation of application No. 17/133,225, filed on Dec. 23, 2020, now Pat. No. 11,723,748.
(Continued)

(51) Int. Cl.
*G06T 15/00* (2011.01)
*A61C 7/00* (2006.01)
(Continued)

(52) U.S. Cl.
CPC ............ *A61C 7/002* (2013.01); *G06N 3/04* (2013.01); *G06N 3/084* (2013.01); *G06T 7/11* (2017.01);
(Continued)

(58) Field of Classification Search
CPC .......... G06T 7/0014; G06T 7/97; G06T 7/12; G06T 7/55; G06T 7/13; G06T 7/11;
(Continued)

(56) References Cited

U.S. PATENT DOCUMENTS

2021/0186659 A1* 6/2021 Li ........................ G06T 17/20
2023/0419631 A1* 12/2023 Ezhov .................. G16H 50/20
(Continued)

OTHER PUBLICATIONS

Wirtz A, Jung F, Noll M, Wang A, Wesarg S. Automatic model-based 3-D reconstruction of the teeth from five photographs with predefined viewing directions. InMedical Imaging 2021: Image Processing Feb. 15, 2021 (vol. 11596, pp. 198-212). SPIE.*
(Continued)

*Primary Examiner* — Phu K Nguyen
(74) *Attorney, Agent, or Firm* — Shay Glenn LLP

(57) ABSTRACT

Provided herein are systems and methods for optimizing a 3D model of an individual's teeth. A 3D dental model may be reconstructed from 3D parameters. A differentiable renderer may be used to derive a 2D rendering of the individual's dentition. 2D image(s) of an individual's dentition may be obtained, and features may be extracted from the 2D image(s). Image loss between the 2D rendering and the 2D image(s) can be derived, and back-propagation from the image loss can be used to calculate gradients of the loss to optimize the 3D parameters. A machine learning model can also be trained to predict a 3D dental model from 2D images of an individual's dentition.

21 Claims, 12 Drawing Sheets

Related U.S. Application Data

(60) Provisional application No. 62/952,850, filed on Dec. 23, 2019.

(51) Int. Cl.
| | | |
|---|---|---|
| *G06N 3/04* | (2023.01) | |
| *G06N 3/084* | (2023.01) | |
| *G06T 7/00* | (2017.01) | |
| *G06T 7/11* | (2017.01) | |
| *G06T 7/13* | (2017.01) | |
| *G06T 17/20* | (2006.01) | |
| *G06T 19/20* | (2011.01) | |
| *G16H 20/40* | (2018.01) | |
| *G16H 30/40* | (2018.01) | |
| *G16H 50/50* | (2018.01) | |

(52) U.S. Cl.
CPC .................. *G06T 7/13* (2017.01); *G06T 7/97* (2017.01); *G06T 17/20* (2013.01); *G06T 19/20* (2013.01); *G16H 20/40* (2018.01); *G16H 30/40* (2018.01); *G16H 50/50* (2018.01); *A61C 2007/004* (2013.01); *G06T 2207/20081* (2013.01); *G06T 2207/20084* (2013.01); *G06T 2207/30036* (2013.01); *G06T 2210/41* (2013.01); *G06T 2210/56* (2013.01)

(58) Field of Classification Search
CPC ..................... G06T 17/20; G06T 19/20; G06T 2207/20224; G06T 2207/10116; G06T 2207/20081; G06T 2210/56; G06T 2210/41; G06T 2207/20084; G06T 2207/20076; G06T 2207/10048; G06T 2207/20072; G06T 2207/30036; G16H 20/40; G16H 50/50; G16H 30/40; A61C 7/002; A61C 2007/004; G06N 3/084; G06N 3/04
USPC ......................................................... 345/418
See application file for complete search history.

(56) References Cited

U.S. PATENT DOCUMENTS

2024/0024075 A1* 1/2024 Li ........................ G06T 7/0014
2024/0169532 A1* 5/2024 Avni ........................ G06T 7/11

OTHER PUBLICATIONS

Maken P, Gupta A. 2D-to-3D: a review for computational 3D image reconstruction from X-ray images. Archives of Computational Methods in Engineering. Jan. 2023;30(1):85-114.*

Chen Y, Gao S, Tu P, Chen X. Automatic 3D Teeth Reconstruction from Five Intra-oral Photos Using Parametric Teeth Model. IEEE Transactions on Visualization and Computer Graphics. May 19, 2023.*

Wu C, Bradley D, Garrido P, Zollhofer M, Theobalt C, Gross MH, Beeler T. Model-based teeth reconstruction. ACM Trans. Graph . . . Nov. 11, 2016;35(6):220-1.*

Ronneberger O, Fischer P. Brox T. U-net: Convolutional networks for biomedical image segmentation. InMedical image computing and computer-assisted intervention—MICCAI 2015: 18th international conference, Munich, Germany, Oct. 5-9, 2015, proceedings, part III 18 2015 (pp. 234-241). Springer International Publish.*

Chen LC, Zhu Y, Papandreou G, Schroff F, Adam H. Encoder-decoder with atrous separable convolution for semantic image segmentation. InProceedings of the European conference on computer vision (ECCV) 2018 (pp. 801-818).*

* cited by examiner

FIG. 2A
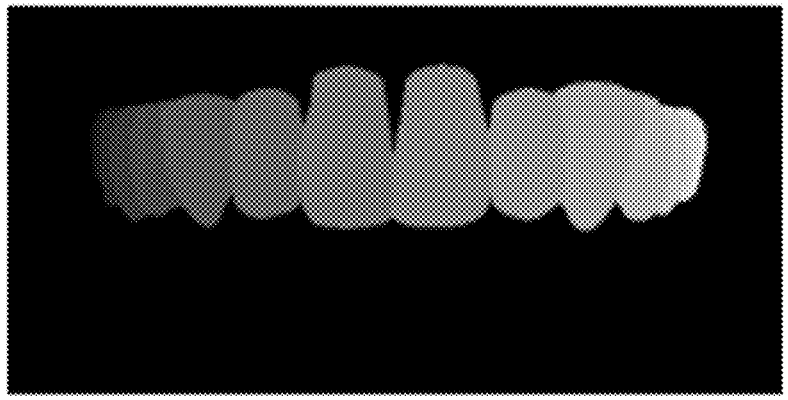
FIG. 2B
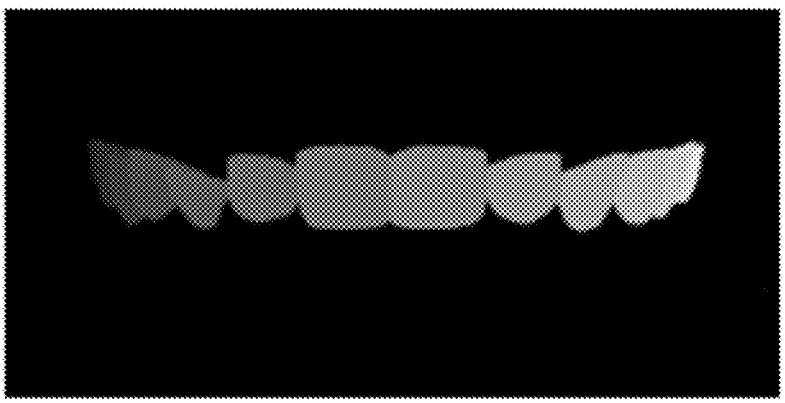
FIG. 2C    FIG. 2D
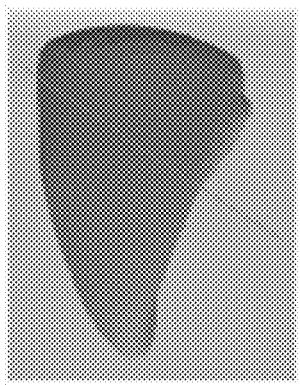 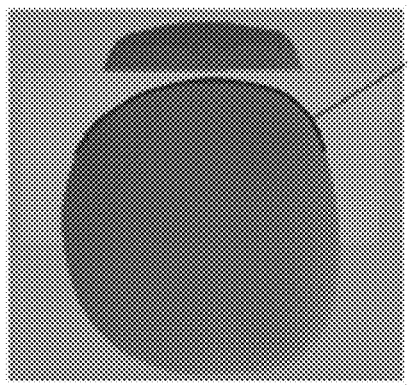
FIG. 2E
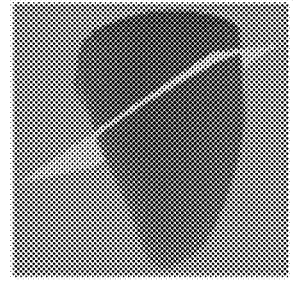

METHODS AND SYSTEMS FOR FORMING A THREE-DIMENSIONAL MODEL OF DENTITION

CROSS REFERENCE TO RELATED APPLICATIONS

This patent application is a continuation of U.S. patent application Ser. No. 17/133,225, titled "2D-TO-3D TOOTH RECONSTRUCTION, OPTIMIZATION, AND POSITIONING FRAMEWORKS USING A DIFFERENTIABLE RENDERER," filed on Dec. 23, 2020, now U.S. Patent Application Publication No. 2021/0186659, which claims priority to U.S. Provisional Patent Application No. 62/952,850, titled "2D-TO-3D TOOTH RECONSTRUCTION, OPTIMIZATION, AND POSITIONING FRAMEWORKS USING A DIFFERENTIABLE RENDERER," filed on Dec. 23, 2019, each of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Orthodontic procedures typically involve repositioning an individual's teeth to a desired arrangement in order to correct malocclusions and/or improve aesthetics. To achieve these objectives, orthodontic appliances such as braces, shell aligners, and the like can be applied to the individual's teeth by an orthodontic practitioner and/or by the individuals themselves. The appliance can be configured to exert force on one or more teeth in order to effect desired tooth movements according to a treatment plan.

Orthodontic aligners may include devices that are removable and/or replaceable over the teeth. Orthodontic aligners may be provided as part of an orthodontic treatment plan. In some orthodontic treatment plans involving removable and/or replaceable aligners, an individual may be provided a plurality of orthodontic aligners over the course of treatment to make incremental position adjustments to the individual's teeth. An orthodontic aligner may have a polymeric trough with an inner cavity shaped to receive and resiliently reposition teeth from one tooth arrangement to a successive tooth arrangement. Orthodontic aligners may include "active" regions that impose repositioning forces on teeth and "passive" regions that retain teeth in their current state.

Treatment planning typically uses a 3D dental model created from a scan or dental mold of an individual's teeth. The 3D dental model can comprise, for example, raw tooth point clouds, tooth meshes, or reduced parameter representations of 3D teeth. These 3D models are often computer/resource intensive to compute and manipulate, and can be difficult to present to an individual.

An expectation maximization (EM) approach can be used to convert a 2D image or images into a 3D model. In this context, an EM algorithm can be used as an iterative technique in which each variable is optimized individually at each step of the algorithm to find 3D models whose 2D rendering most closely matches the 2D image under consideration.

SUMMARY OF THE DISCLOSURE

Implementations address the need to improve the accuracy and efficiency of generating 3D models of an individual's dentition and positioning 3D models of the individual's dentition. The present application addresses these and other technical problems by providing technical solutions and/or automated agents that automatically optimize 3D dental models. In one implementation, a 3D geometry optimization framework is provided that includes automated agents configured to use differential rendering techniques on a 3D dental model to form 2D image(s), which are compared against original 2D images of the individual's teeth to update or improve the 3D dental model. The 3D dental model can comprise, for example, raw tooth point clouds, tooth meshes, or reduced parameter representations of 3D teeth such as PCA representations. The rendered 2D images can be compared against the original 2D images of the individual's teeth to derive image loss (difference between images). Back propagation can then be conducted from the image loss to calculate derivatives or gradients of the loss with respect to the 3D model parameters.

Implementations herein also address the need to provide an automated system to automatically, effectively, and accurately form a 3D model or 3D mesh of an individual's detention from 2D photos of the individual's teeth. The present application addresses these and other technical problems by providing technical solutions and/or automated agents that train machine learning neural networks to reconstruct a 3D dental model from one or more 2D images of the individual's teeth. In one implementation, automated agents are configured to use differential rendering techniques on a 3D dental model to form 2D image(s), which are compared against original 2D images of the individual's teeth. The neural network can be trained to predict 3D dentition model parameters which leads to 3D dentition models that best match with 2D images. Once the machine learning neural network is properly trained, it can be used to construct 3D dental models directly from one or more 2D images of the individual's teeth.

In general, example apparatuses (e.g., devices, systems, etc.) and/or methods described herein may acquire a representation of an individual's teeth. The representation may be a plurality of 2D images or digital photographs of the individual's teeth. As used herein, an individual may be a patient with or without a diagnosed ailment (e.g., an orthodontic patient, a dental patient, etc.). The methods and apparatuses (e.g., systems) described herein may be used for developing or refining a treatment plan for an individual (e.g., a patient).

In general, example apparatuses (e.g., devices, systems, etc.) and/or methods described herein may train a machine learning model to create a 3D dental model from an input comprising one or more 2D images of the individual's teeth. Examples of machine learning systems that may be used include, but are not limited to, Neural Networks (primarily Convolutional Neural Networks (CNN)), Decision Tree, Random Forest, Logistic Regression, Support Vector Machine, AdaBoosT, K-Nearest Neighbor (KNN), Quadratic Discriminant Analysis, etc.

Any of the apparatuses and/or methods described herein may be part of a distal tooth scanning apparatus or method, or may be configured to work with a digital scanning apparatus or method.

In some implementations, the 3D model can include automatic tooth segmentation that may provide the basis for implementation of automated orthodontic treatment plans, design and/or manufacture of orthodontic aligners (including series of polymeric orthodontic aligners that provide forces to correct malocclusions in an individual's teeth). These apparatuses and/or methods may provide or modify a treatment plan, including an orthodontic treatment plan. The apparatuses and/or methods described herein may provide instructions to generate and/or may generate a set or series of aligners, and/or orthodontic treatment plans using orthodontic aligners that incorporate post-treatment tooth position scoring. The apparatuses and/or methods described herein may provide a visual representation of the individual's post-treatment tooth positions.

For example, described herein are methods of forming a 3D dental model of an individual's dentition. These methods may include: (1) obtaining an set of 3D parameters for the individual's dentition; (2) constructing a parametric 3D dental model of the individual's dentition with the set of 3D parameters; (3) applying a differentiable renderer to the parametric 3D dental model to derive a 2D rendering of the individual's dentition; (4) obtaining an original 2D image of the individual's dentition; (5) extracting features from the original 2D image; (6) comparing the 2D rendering to the extracted features to derive an image loss function from a difference of the original 2D image and the 2D rendering at each pixel location; (7) performing back-propagation from the image loss function to calculate gradients of loss with respect to the set of 3D parameters; (8) updating the set of 3D parameters based on the calculated gradients; (9) revising the parametric 3D dental model of the individual's dentition with the updated set of 3D parameters; and (10) outputting the parametric 3D dental model.

Although the steps above are enumerated, in some variations the order of these steps may be varied, as indicated herein. In particular steps that do not require information from a prior step may be performed before or after the prior step. For example the steps of obtaining the 2D images from the individual's dentition and extracting features from these original images may be done before the step of comparing these extracted features.

Any of the methods described herein may result in outputting of the 3D dental model (e.g., the parametric 3D dental model). The 3D model may be output to a display (e.g., screen, monitor, etc.), and/or to a memory (e.g., digital storage media), and/or transmitted.

In general, the methods described herein may include repeating the steps (e.g., repeating steps 3-9, above) until convergence. For example, until the 2D rendering converges with the extracted features. The 2D rendering may converge with the extracted features within a predetermined threshold (e.g. until the difference is less than 0.001, less than 0.01, less than 0.1, less than 1, less than 5, etc.).

The parametric 3D dental model may comprise a tooth mesh (e.g., a mesh model of a tooth or teeth). The parametric 3D dental model may comprise a point cloud model (e.g., a tooth point cloud, or a point cloud model of a tooth or teeth). The parametric 3D dental model may comprise a reduced representation of a 3D dental model, such as a principal component analysis representation.

In some variations, the extracted features comprise tooth masks for the upper/lower jaws. The extracted features may comprise tooth segmentation data and/or numbering data. The extracted features may comprise dental edge information.

Any of the methods described herein may be performed using machine learning (e.g., using a neural network). For example, also described herein are methods of training a machine learning model to generate a 3D dental model, comprising: optionally obtaining a ground truth set of 3D parameters for the individual's dentition; constructing a parametric 3D dental model of the individual's dentition with a set of machine learning model parameters; applying a differentiable renderer to the parametric 3D dental model to derive a 2D rendering of the individual's dentition; obtaining a 2D image of the individual's dentition; extracting features from the 2D image; comparing the 2D rendering to the extracted features to derive an image loss function at each pixel location; performing back-propagation from the image loss function to calculate gradients of loss with respect to the neural network parameters and update the neural network parameters based on the calculated gradients; and training a machine learning model to predict 3D parameters using the extracted features, the ground truth set of 3D parameters, and the updated set of 3D parameters.

As mentioned, the parametric 3D dental model may comprise a tooth mesh, a tooth point cloud; and/or a principal component analysis representation. The extracted features may comprise tooth masks for the upper/lower jaws, and/or tooth segmentation data, and/or dental edge information.

A method of training a machine learning model to form a three-dimensional (3D) dental model may include: (1) obtaining a ground truth set of 3D parameters for the patient's dentition, and/or 3D dentition models; (2) obtaining a set of 2D images of the patient's dentition; (3) extracting features from the set of 2D images; (4) initializing the machine learning model with network weights; (5) constructing a parametric 3D dental model of the patient's dentition with the machine learning model; (6) applying a differentiable renderer to the parametric 3D dental model to derive a 2D rendering of the patient's dentition; (7) comparing the 2D rendering to the extracted features from the set of 2D images at each pixel location to derive a loss function; (8) calculating the final loss using the loss function; (9) back-propagating from the final loss to calculate gradients of loss with respect to network weights; (10) updating the network weights based on the gradients of loss; (11) repeating steps 5-11 until the 2D rendering converges with the extracted features; and (12) outputting the parametric 3D dental model.

In some examples, the loss function may also include a comparison between the predicted 3D dentition parameters and ground truth dentition parameters, or between 3D reconstructed dentition and the ground truth 3D dentition.

The network weights may be initialized randomly.

Any of these methods may include calculating a 3D parameter loss by comparing predicted 3D parameters from the parametric 3D dental model with the ground truth set of 3D parameters; the step of calculating the final loss may comprise using the 3D parameter loss.

Any of these methods may include calculating a 3D dental model loss by comparing the parametric 3D dental model with a ground truth 3D dental model; the step of calculating the final loss may comprise using the 3D dental model loss.

The parametric 3D dental model may include a reduced representation of a 3D dental model. The reduced representation of the 3D dental model may comprise a principal component analysis representation, as mentioned above. The extracted features may include tooth segmentation and/or numbering data.

Also described herein are methods of making and using any of the machine learning models (e.g., neural networks) described. In general, described herein are methods of using a trained machine learning model, comprising: inputting an original 2D image of an individual's dentition into the trained machine learning model; and outputting a parametric 3D dental model of the individual's dentition from the trained machine learning model.

Any of the methods described herein may be implemented as software, firmware, and/or hardware, and may be included as part of a system (e.g., a system for forming a 3D model of dentition). The system may include one or more processors and memory holding instructions comprising one or more of the methods described herein. For example, a system for forming a 3D dental model of an individual's dentition may include: one or more processors; and a memory coupled to the one or more processors, the memory configured to store computer-program instructions, that, when executed by the one or more processors, perform a computer-implemented method comprising: (1) obtaining a set of 3D parameters for the individual's dentition; (2) constructing a parametric 3D dental model of the individual's dentition with the set of 3D parameters; (3) applying a differentiable renderer to the parametric 3D dental model to derive a 2D rendering of the individual's dentition; (4) obtaining an original 2D image of the individual's dentition; (5) extracting features from the original 2D image; (6) comparing the 2D rendering to the extracted features to derive an image loss function from a difference of the original 2D image and the 2D rendering at each pixel location; (7) performing back-propagation from the image loss function to calculate gradients of loss with respect to the set of 3D parameters; (8) updating the set of 3D parameters based on the calculated gradients; (9) revising the parametric 3D dental model of the individual's dentition with the updated set of 3D parameters; and (10) outputting the parametric 3D dental model. The method may further comprise repeating steps 3-9 until the 2D rendering converges with the extracted features within a predetermined threshold.

A system for training a machine learning model to form a three-dimensional (3D) dental model may include: one or more processors; and a memory coupled to the one or more processors, the memory configured to store computer-program instructions, that, when executed by the one or more processors, perform a computer-implemented method comprising: (1) obtaining a ground truth set of 3D parameters for the patient's dentition, and/or 3D dentition models; (2) obtaining a set of 2D images of the patient's dentition; (3) extracting features from the set of 2D images; (4) initializing the machine learning model with network weights; (5) constructing a parametric 3D dental model of the patient's dentition with the machine learning model; (6) applying a differentiable renderer to the parametric 3D dental model to derive a 2D rendering of the patient's dentition; (7) comparing the 2D rendering to the extracted features from the set of 2D images at each pixel location to derive a loss function; (8) calculating the final loss using the loss function; (9) back-propagating from the final loss to calculate gradients of loss with respect to network weights; (10) updating the network weights based on the gradients of loss; (11) repeating steps 5-11 until the 2D rendering converges with the extracted features; and (12) outputting the parametric 3D dental model.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A-2E show examples of one technique for simulating a gingiva line in a 3D dental model.

DETAILED DESCRIPTION

Figure 1A:
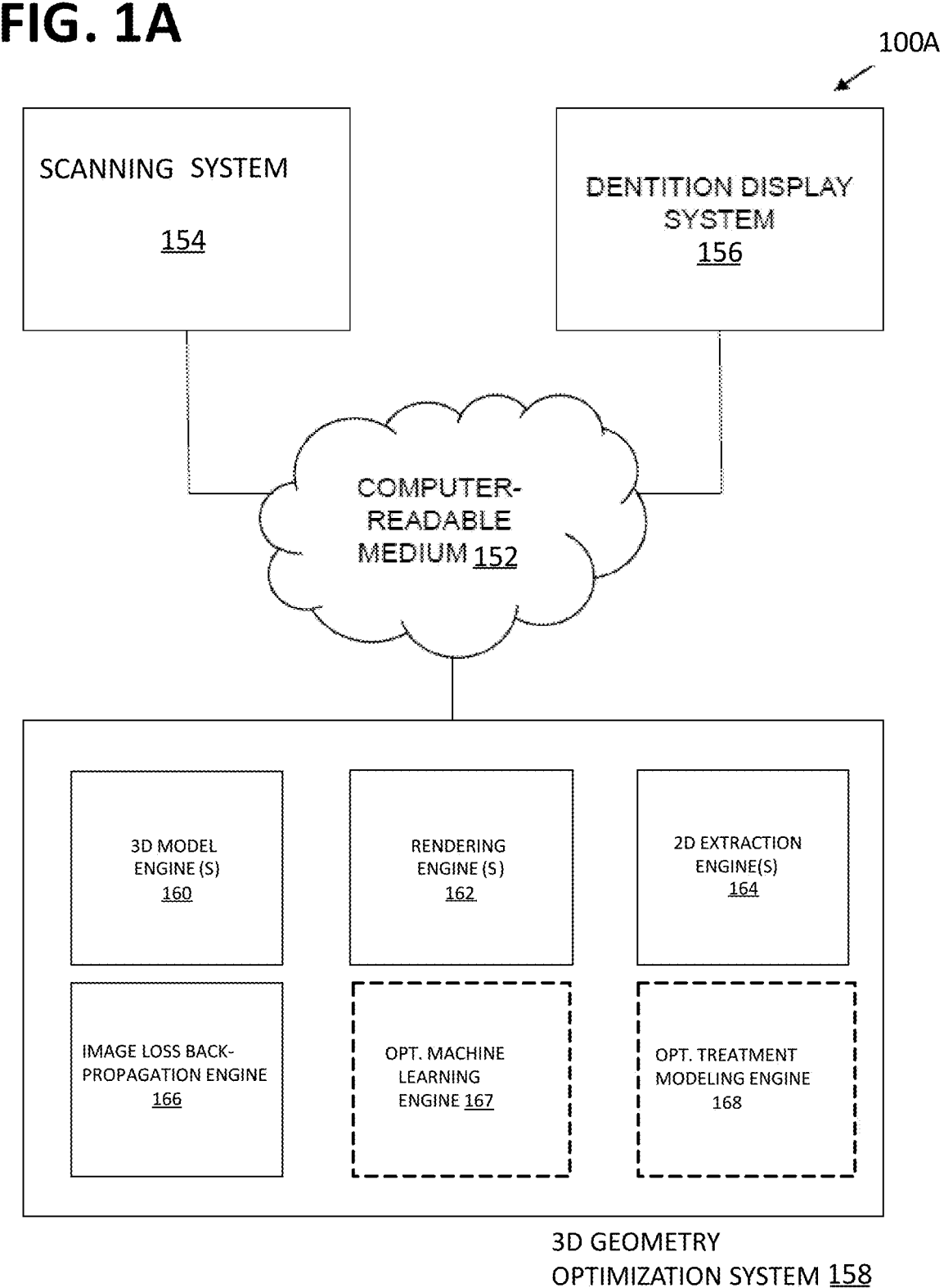
FIG. 1A is a diagram showing an example of a computing environment configured to digitally scan a dental arch and determine a post-treatment tooth position score.

Described herein are apparatuses (e.g., systems, computing device readable media, devices, etc.) and methods for implementing a 3D geometry optimization framework that uses differentiable rendering techniques to improve, update, and optimize a 3D dental model. The apparatuses and methods described herein can use a differentiable renderer to form 2D images from a 3D dental model, which can then be compared against original 2D images of the individual's teeth to update or improve the 3D dental model. In some implementations, the rendered 2D images are compared against the original 2D images (or tooth edges, tooth segmentation masks, etc.) to derive image loss. The apparatuses and methods described herein can then be configured to conduct back propagation from the image loss to calculate derivatives or gradients of the loss with respect to the 3D model parameters, which can then be utilized in optimization algorithms to improve the 3D modeling.

Also described herein are apparatuses and methods for training a machine learning neural network to reconstruct a 3D dental model from one or more 2D images of an individual's teeth. In one implementation, automated agents are configured to use differentiable rendering techniques on a 3D dental model to form 2D image(s), which are compared against original 2D images of the individual's teeth to create an image loss function. The neural network can be trained to predict 3D dentition model parameters, which leads to a 3D dentition model that minimizes the image loss function. Once the machine learning neural network is properly trained, it can be used to construct 3D dental models directly from one or more 2D images of the individual's teeth.

The machine learning models described herein can be trained to construct 3D models based upon data including individual demographics, tooth measurements, tooth surface mesh, processed tooth features, and historical patient data.

These methods and apparatus can use this information to train a machine learning model and use the machine learning model to create a 3D model of the individual's detention.

The apparatuses and/or methods described herein may be useful in planning and fabrication of dental appliances, including elastic polymeric positioning appliances, is described in detail in U.S. Pat. No. 5,975,893, and in published PCT application WO 98/58596, which is herein incorporated by reference for all purposes. Systems of dental appliances employing technology described in U.S. Pat. No. 5,975,893 are commercially available from Align Technology, Inc., Santa Clara, Calif., under the tradename, Invisalign System.

Throughout the body of the Description of Embodiments, the use of the terms "orthodontic aligner", "aligner", or "dental aligner" is synonymous with the use of the terms "appliance" and "dental appliance" in terms of dental applications. For purposes of clarity, embodiments are hereinafter described within the context of the use and application of appliances, and more specifically "dental appliances."

An "individual," as used herein, may be any subject (e.g., human, non-human, adult, child, etc.) and may be alternatively and equivalently referred to herein as a "patient", a "patient under treatment", or a "subject." A "patient," as used herein, may but need not be a medical patient. An "individual" or a "patient," as used herein, may include a person who receives orthodontic treatment, including orthodontic treatment with a series of orthodontic aligners.

The apparatuses and/or methods (e.g., systems, devices, etc.) described below can be used with and/or integrated into an orthodontic treatment plan. The apparatuses and/or methods described herein may be used to segment an individual's teeth from a three-dimensional model, such as a 3D mesh model or a 3D point cloud, and this segmentation information may be used to simulate, modify and/or choose between various orthodontic treatment plans. Segmenting the individual's teeth can be done automatically (e.g., using a computing device). For example, segmentation can be performed by a computing system automatically by evaluating data (such as three-dimensional scan, or a dental impression) of the individual's teeth or arch.

As described herein, an intraoral scanner may image an individual's dental arch and generate a virtual three-dimensional model of that dental arch. During an intraoral scan procedure (also referred to as a scan session), a user (e.g., a dental practitioner) of an intraoral scanner may generate multiple different images (also referred to as scans or medical images) of a dental site, model of a dental site, or other object. The images may be discrete images (e.g., point-and-shoot images) or frames from a video (e.g., a continuous scan).

FIG. 1A is a diagram showing an example of a computing environment 100A configured to facilitate gathering and processing digital scans of a dental arch with teeth therein. The environment 100A includes a computer-readable medium 152, a scanning system 154, a dentition display system 156, and a 3D geometry optimization system 158. One or more of the modules in the computing environment 100A may be coupled to one another or to modules not explicitly shown.

The computer-readable medium 152 and other computer readable media discussed herein are intended to represent a variety of potentially applicable technologies. For example, the computer-readable medium 152 can be used to form a network or part of a network. Where two components are co-located on a device, the computer-readable medium 152 can include a bus or other data conduit or plane. Where a first component is co-located on one device and a second component is located on a different device, the computer-readable medium 152 can include a wireless or wired back-end network or LAN. The computer-readable medium 152 can also encompass a relevant portion of a WAN or other network, if applicable.

The scanning system 154 may include a computer system configured to scan an individual's dental arch. A "dental arch," as used herein, may include at least a portion of an individual's dentition formed by the individual's maxillary and/or mandibular teeth, when viewed from an occlusal perspective. A dental arch may include one or more maxillary or mandibular teeth of an individual, such as all teeth on the maxilla or mandible or an individual. The scanning system 154 may include memory, one or more processors, and/or sensors to detect contours on an individual's dental arch. The scanning system 154 may be implemented as a camera, an intraoral scanner, an x-ray device, an infrared device, etc. In some implementations, the scanning system 154 is configured to produce 3D scans of the individual's dentition. In other implementations the scanning system 154 is configured to produce 2D scans or images of the individual's dentition. The scanning system 154 may include a system configured to provide a virtual representation of a physical mold of patient's dental arch. The scanning system 154 may be used as part of an orthodontic treatment plan. In some implementations, the scanning system 154 is configured to capture an individual's dental arch at a beginning stage, an intermediate stage, etc. of an orthodontic treatment plan. The scanning system 154 may be further configured to receive 2D or 3D scan data taken previously or by another system.

The dentition display system 156 may include a computer system configured to display at least a portion of a dentition of an individual. The dentition display system 154 may include memory, one or more processors, and a display device to display the individual's dentition. The dentition display system 156 may be implemented as part of a computer system, a display of a dedicated intraoral scanner, etc. In some implementations, the dentition display system 156 facilitates display of an individual's dentition using scans that are taken at an earlier date and/or at a remote location. It is noted the dentition display system 156 may facilitate display of scans taken contemporaneously and/or locally to it as well. As noted herein, the dentition display system 156 may be configured to display the intended or actual results of an orthodontic treatment plan applied to a dental arch scanned by the scanning system 154. The results may include 3D virtual representations of the dental arch, 2D images or renditions of the dental arch, etc.

The 3D geometry optimization system 158 may include a computer system, including memory and one or more processors, configured to optimize a 3D model of an individual's dentition. In one implementation, the 3D geometry optimization system is configured to process scan data from the scanning system 154. In some examples, 2D scan data, such as one or more photos representing the individual's dentition, may be processed to extract relevant information such as upper/lower jaw masking, tooth segmentation information, and/or tooth edge information. The 3D geometry optimization system can be further configured to obtain initial 3D parameters for the 3D model of the individual's dentition. In one example, the initial 3D parameters can comprise mean 3D parameter values for similar patients acquired from historical patient data. The 3D geometry optimization system can be configured to construct a 3D dental model of the individual's dentition from the initial 3D parameters. In one implementation, the 3D geometry optimization system is further configured to use a differentiable renderer on the 3D dental model to derive 2D rendering(s) of the individual's dentition. The 2D renderings of the individual's dentition can be compared to original 2D images of the individual's teeth (such as 2D camera images, and/or the aforementioned processed 2D images such as tooth segmentation masks and edges, etc.) to derive image loss. In one implementation, the 3D geometry optimization system can use gradient back-propagation from the image loss to the 3D parameters to allow direct 3D shape parameter optimization without an iterative expectation-maximization approach. A new 3D dental model can be constructed with the optimized 3D parameters. The 3D geometry optimization system 158 may include 3D model engine(s) 160, rendering engine(s) 162, 2D extraction engine(s) 164, image loss back-propagation engine(s) 166, and optional treatment modeling engine(s) 168. One or more of the modules of the 3D geometry optimization system 158 may be coupled to each other or to modules not shown.

The 3D model engine(s) 160 of the 3D geometry optimization system 158 may implement automated agents to produce 3D dental models of the individual's dentition, with or without a real or simulated gingiva line. The 3D dental models may include 3D tooth shape representations in the form of a tooth point cloud, a tooth mesh, or a reduced parameter representation. In one example, a principal component analysis (PCA) can be implemented to obtain the reduced parameter representation. For example, PCA can be applied to a tooth point cloud or a tooth mesh to obtain eigenvectors (alternatively, a "representation") which capture most tooth shape variance. In some implementations, an initial 3D dental model can be created with initial 3D parameters selected by the 3D model engine. In one implementation, the initial 3D parameters can be mean 3D parameters acquired from historical patient data. The historical patient data can be filtered based on patient information including age, race, gender, etc. In some implementations, the 3D parameters can include 3D tooth shape parameters (e.g., a 3D dental mesh, a 3D point cloud, PCA parameters), camera/scanning system parameters, 3D tooth location parameters, and 3D tooth orientation parameters. The 3D model engine(s) 160 can further create subsequent iterations of the 3D dental model with updated/optimized 3D parameters determined by the image loss back-propagation engine(s) 166, as described below. The image loss back-propagation engine(s) 166 can repeatedly update/optimize 3D parameters and eventually create an optimized 3D dental model.

The rendering engine(s) 162 of the 3D geometry optimization system 158 may implement automated agents to render one or more 2D images from a 3D dental model of an individual's dentition in a mathematically differentiable manner. For example, the rendering engine(s) 162 may be configured to render 2D images with a differentiable renderer from the initial 3D dental model produced by the 3D model engine(s) 160 above. The rendered 2D images can comprise, for example, rendered images through a differentiable renderer of the individual's dentition, or alternatively, of individual teeth or dental features of the individual's dentition from the 3D dental model. The differentiable renderer enables a process for creating 2D images from the 3D dental model that is mathematically continuous and differentiable.

The 2D extraction engine(s) 164 of the 3D geometry optimization system 158 can implement automated agents to extract features from original 2D images of the individual's dentition. The original 2D images can be obtained, for example, with the scanning system 154 as described above. The 2D extraction engine(s) 164 can be configured to extract features from the original 2D images, including tooth masks for the upper and lower jaws, tooth segmentation information including identification of individual teeth and/or tooth types, and dental edge information including tooth edges and gingiva lines.

The image loss back-propagation engine(s) 166 of the 3D geometry optimization system 158 can implement automated agents to compare the rendered 2D image(s) from the rendering engine(s) 162 to the extracted features from the 2D extraction engine(s) 164. The image loss back-propagation engine(s) 166 can be configured to compare pixel values between the rendered 2D images and the extracted features and aggregate the difference at each pixel location into a single image loss function. Since the image loss is a continuous function of all the 3D parameters used to form the initial 3D dental model, the image loss back-propagation engine(s) 166 can be further configured to compute derivatives/gradients of the loss with respect to 3D tooth shape parameters, 3D tooth location parameters, 3D tooth orientation parameters, and camera/scanning system parameters. This gradient calculation reveals exactly how the rendered 2D images from the rendering engine will change when varying any of the 3D parameters of the 3D dental model in the 3D model engine. Thus, the image loss back-propagation engine(s) 166 enables gradient back-propagation from the rendered 2D image(s) to 3D tooth geometry parameters (and camera/scanner parameters), allowing for direct parameter optimization. The image loss back-propagation engine(s) 166 can therefore provide updated/optimized 3D parameters to the 3D model engine to improve the accuracy of the 3D dental model.

The machine learning engine(s) 167 may implement automated agents to train a machine learning model to predict 3D dental models from original 2D images of an individual's dentition. The machine learning engine(s) 167 can be trained to predict 3D dental models using either original 2D images or extracted features from the 2D original images, and with or without ground truth 3D parameters (and/or dental models) for patients' dentitions from historical patient data along with the aforementioned image loss (and potentially some additional loss functions as well). For example, the ground truth 3D parameters can comprise 3D parameters acquired from historical patient data for a certain population. The historical patient data can be filtered for that population based on patient information including age, race, gender, etc. The ground truth 3D parameters for a certain population can be used to construct a ground truth dataset. A machine learning model can be trained to predict 3D parameters from original 2D images. These predicted 3D parameters can then be used in three successive stages: (1) directly compare predicted 3D parameters with the ground truth 3D parameters; (2) reconstruct 3D dental models from the predicted 3D parameters through the 3D model engine 160, and compare reconstructed 3D dental models with ground truth dental models; (3) render the reconstructed 3D dental model through the differentiable rendering engine 162 to obtain a rendered image, and compare it to the original 2D image through the image loss engine 166. It should be noted that stages 1-2 above are optional. The comparisons in the aforementioned three stages can then be aggregated into a single loss function to supervise the training process of the machine learning model through a back-propagation optimization process. The trained machine learning model may be configured to automatically predict 3D parameters directly from original 2D images of the individual's dentition.

Examples of machine learning systems that may be used include, but are not limited to, Neural Networks (primarily Convolutional Neural Networks (CNN)), Decision Tree, Random Forest, Logistic Regression, Support Vector Machine, AdaBoosT, K-Nearest Neighbor (KNN), Quadratic Discriminant Analysis, etc.

The optional treatment modeling engine(s) 168 may be configured to use the optimized 3D model to store and/or provide instructions to implement orthodontic treatment plans and/or the results of orthodontic treatment plans. The optional treatment modeling engine(s) 168 may provide the results of orthodontic treatment plans on the optimized 3D dental model. In some embodiments, the optimized 3D dental model can be rendered into one or more 2D image(s) from a plurality of viewing angles. The optional treatment modeling engine(s) 168 may model the results of application of orthodontic aligners to the individual's dental arch over the course of an orthodontic treatment plan.

As used herein, any "engine" may include one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, "datastores" may include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

Figure 1B:
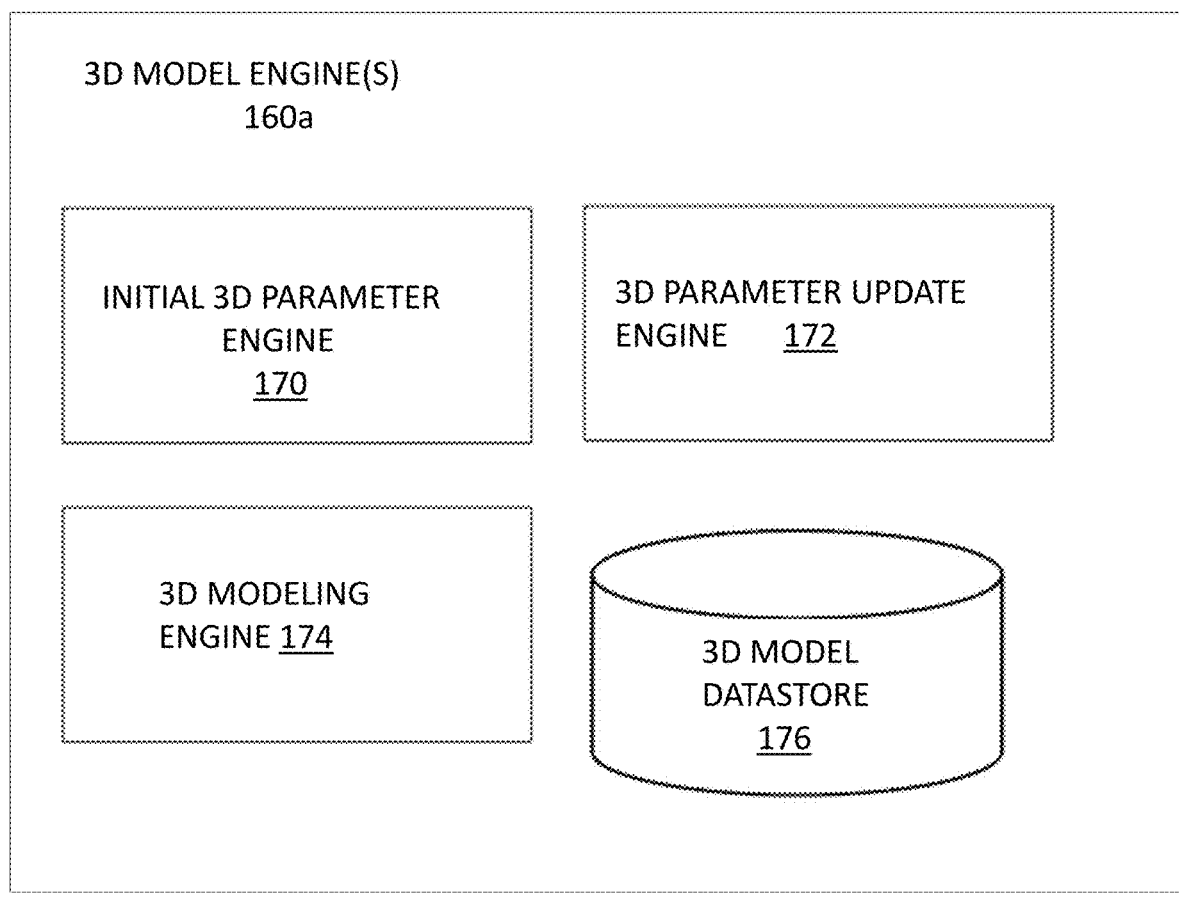
FIG. 1B is a diagram showing an example of 3D model engine(s).

FIG. 1B is a diagram showing an example of the 3D model engine(s) 160a. The 3D model engine(s) 160a may include an initial 3D parameter engine 170, a 3D parameter update engine 172, a 3D modeling engine 174, and a 3D model datastore 176. One or more of the modules of the 3D model engine(s) 160a may be coupled to each other or to modules not shown.

The initial 3D parameter engine 170 may implement one or more automated agents configured to provide an initial set of 3D parameters for construction into a 3D dental model. The 3D parameters can include 3D tooth shape parameters (e.g., a 3D dental mesh, a 3D point cloud, PCA parameters), camera/scanning system parameters (e.g., focal length, pixel density, contrast, exposure, camera/scanner location and orientation, etc.), 3D tooth location parameters, and 3D tooth orientation parameters. The initial set of 3D parameters can be, for example, the average 3D parameters for a 3D dental model from historical patient data. In some implementations, the average 3D parameters can be selected from only historical patient data that represents the individual to be modeled. For example, the mean 3D parameters for similar patients, including patients of similar age, race, gender, etc., can be chosen as the initial set of 3D parameters. The initial set of 3D parameters can be provided to the 3D modeling engine 174 to create the initial 3D dental model as described herein.

The 3D parameter update engine 172 may implement one or more automated agents configured to receive updated/optimized 3D parameters from the image loss back-propagation engine(s) 166. As described above, the 3D parameters can include 3D tooth shape parameters (e.g., a 3D dental mesh, a 3D point cloud, PCA parameters), camera/scanning system parameters (e.g., camera/scanner location/orientation), 3D location parameters, and 3D tooth orientation parameters (e.g., local translation/rotation for each tooth and global translation/rotation for each jaw of the dentition). The updated/optimized 3D parameters will typically be different than the initial set of 3D parameters from the initial 3D parameter engine. Thus, when the updated/optimized 3D parameters are different than the initial set of 3D parameters, the updated/optimized 3D parameters can be provided to the 3D modeling engine 174 to create the optimized 3D dental model as described herein.

The 3D modeling engine 174 may implement one or more automated agents configured to format the initial set of 3D parameters (from initial 3D parameter engine 170) or the updated/optimized 3D parameters (from the 3D parameter update engine 172) into a 3D dental model (e.g., a 3D dental mesh model, a 3D point cloud, a PCA representation etc.) of the dental arch. The 3D model of the dental arch may comprise geometric point clouds or polyhedral objects that depict teeth and/or other elements of the dental arch in a format that can be rendered on the dentition display system 156. In some implementations, the 3D modeling engine 174 may segment the 3D dental model into individual dental components, including individual teeth and/or the gingiva.

In one implementation, the 3D modeling engine 174 can produce a 3D dental model with a simulated gingiva line so that 2D projections of the 3D dental model show only portions of the teeth that would ordinarily be visible, and not portions of the teeth that are covered by gingiva. The simulated gingiva line can be produced by placing a cutting plane through the front of the tooth surface at the intersection of the gingiva and each tooth. In some examples, the cutting plan can be angled as it cuts through the 3D representations of the teeth. FIG. 2A is an example of a projection of a 3D dental model that includes portions of the teeth covered by gingiva. FIG. 2B is an example of a projection of a 3D dental model that includes only the visible portions of the teeth. FIGS. 2C-2E are various views of a cutting plane cutting through 3D models of teeth to produce a simulated gingiva line.

The 3D model datastore 176 may be configured to store data related to the 3D parameters and the 3D dental model, including the initial set of 3D parameters, the updated/optimized 3D parameters, the initial 3D dental model, the optimized 3D dental model, segmentation information, and historical patient data including historical 3D parameters and 3D dental models. In general, one can use a more complicated parametric 3D surface (e.g. a saddle surface) to cut through a 3D tooth, and produce more realistic simulated gingiva lines on both the front and back sides of a tooth at the same time.

Figure 1C:
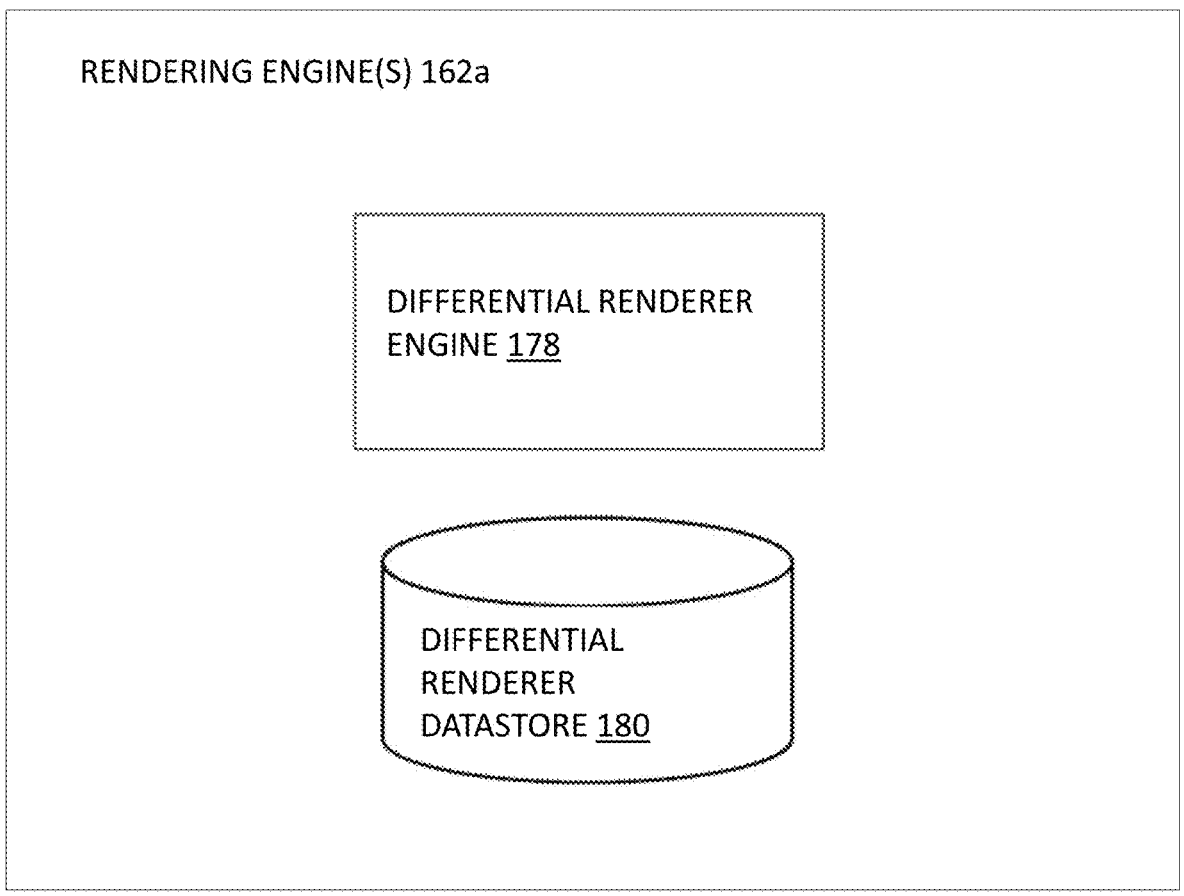
FIG. 1C is a diagram showing an example of rendering engine(s).

FIG. 1C is a diagram showing an example of the rendering engine(s) 162a. The rendering engine(s) 162a may include a differentiable renderer engine 178 and a differentiable renderer datastore 180. One or more of the modules of the rendering engine(s) 162a may be coupled to each other or to modules not shown.

Figure 3A:
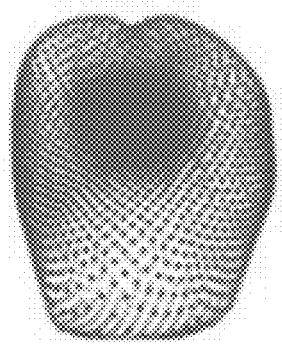
FIGS. 3A-3B illustrate one example of converting a 3D dental model to a differentially rendered 2D image.
Figure 3B:
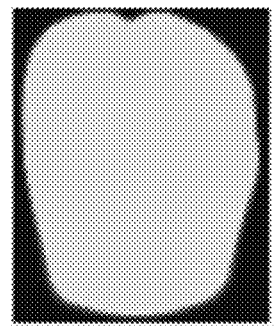

The differentiable renderer engine 178 may implement one or more automated agents configured to render one or more 2D images from a 3D dental model of an individual's dentition in a mathematically differentiable manner. For example, differentiable renderer engine may be configured to render 2D images from the initial 3D dental model produced by the 3D model engine(s) 160 above. The differentiable renderer may further be configured to render 2D images from an updated and/or optimized 3D dental model, as described herein. The rendered 2D images can comprise, for example, rendered images through the differentiable renderer of the individual's dentition, or alternatively, of individual teeth or dental features of the individual's dentition from the 3D dental model. FIG. 3A illustrates one example of a 3D model of an individual tooth (e.g., a 3D mesh or 3D point cloud), and FIG. 3B illustrates an example of a differentially rendered 2D image.

The differentiable renderer datastore 180 may be configured to store data related to the rendered 2D images through the differentiable renderer engine 178.

Figure 1D:
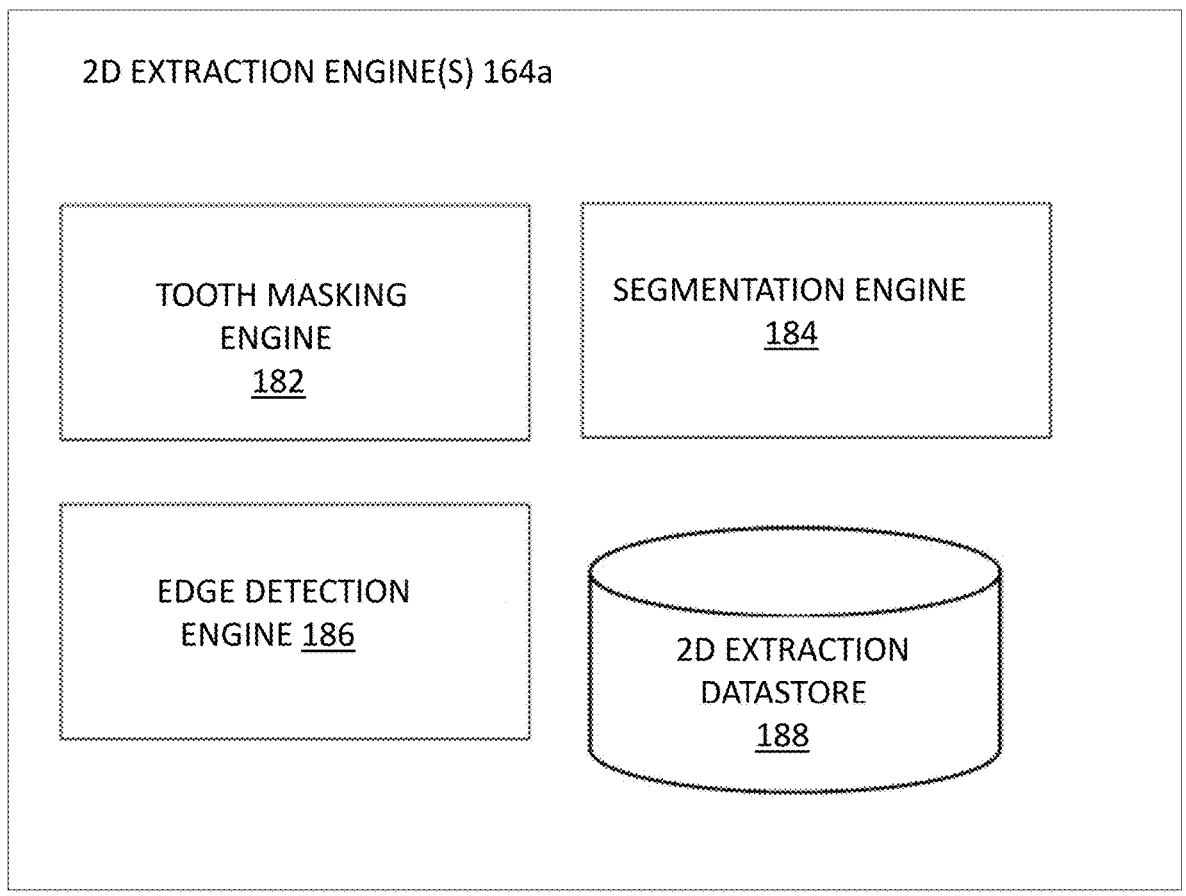
FIG. 1D is a diagram showing an example of a 2D extraction engine(s).

FIG. 1D is a diagram showing an example of the 2D extraction engine(s) 164a. The 2D extraction engine(s) 164a may include a jaw masking engine 182, a segmentation engine 184, an edge detection engine 186, and a 2D extraction datastore 188. One or more of the modules of the 2D extraction engine(s) 164a may be coupled to each other or to modules not shown.

Figure 4A:
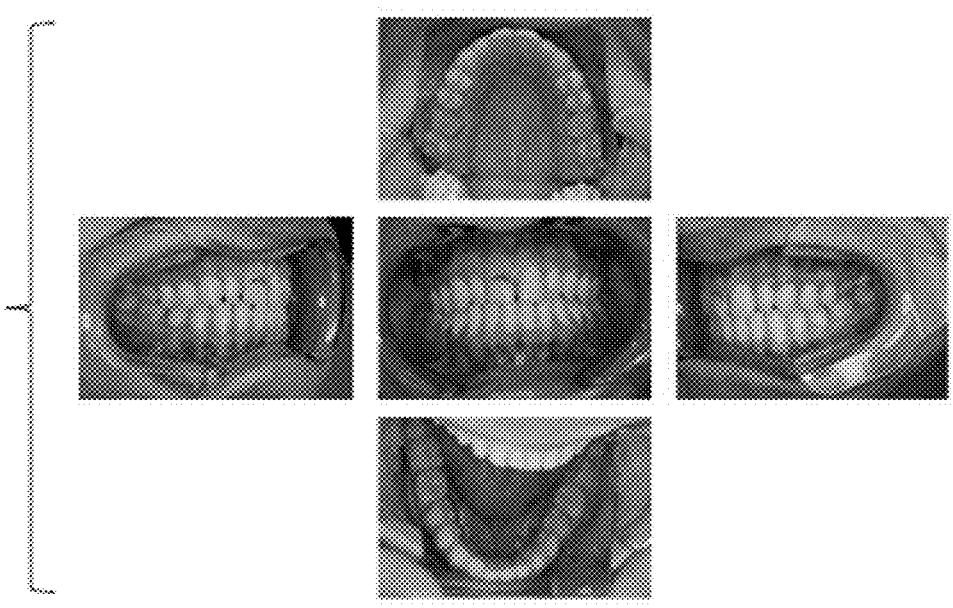
FIGS. 4A and 4B illustrate a set of original 2D images of an individual's dentition and segmentation masks identified from the original 2D images, respectively.
Figure 4B:
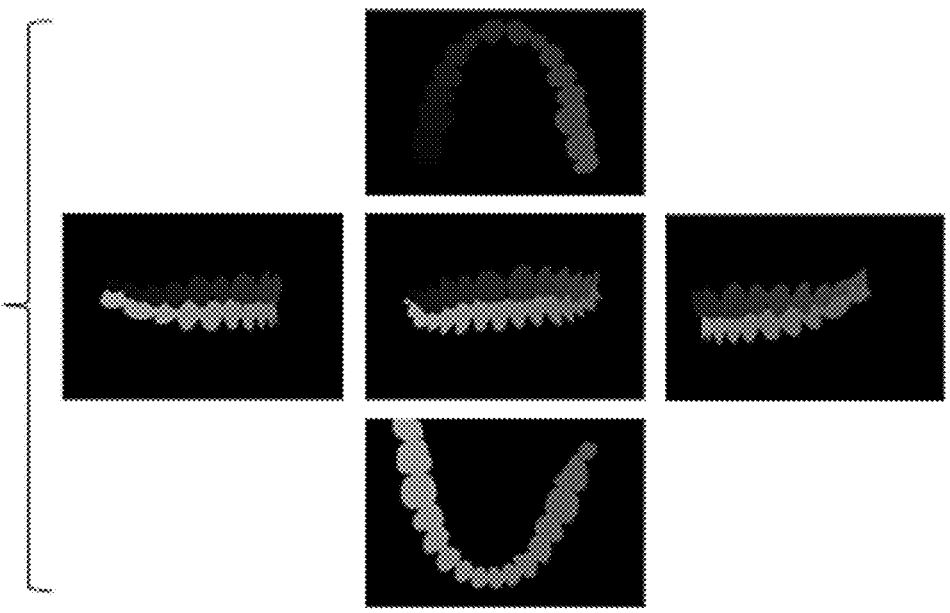

The tooth masking engine 182 may implement one or more automated agents configured to identify segmentation masks from original 2D images of the individual's dentition. The tooth masking engine 182 can identify segmentation masks on the upper and lower jaws of the individual's arch from the original 2D images. The segmentation masks can comprise, for example, 2D representations of data from the original 2D images corresponding to teeth in the individual's arch. The segmentation masks can be identified for both the upper and lower jaws of the individual's arch. FIGS. 4A and 4B illustrate a set of original 2D images of an individual's dentition and segmentation masks identified from the original 2D images, respectively.

The segmentation engine 184 may implement one or more automated agents configured to scan original 2D images of the individual's dentition for individual tooth segmentation data. "Individual tooth segmentation data," as used herein, may include positions, geometrical properties (contours, etc.), and/or other data that can form the basis of segmenting individual teeth from 2D images of an individual's dental arch. The segmentation engine 184 may implement automated agents to separate data for individual teeth from 2D images of the dental arch. The segmentation engine 184 may further implement automated agents to number the individual teeth or identify the tooth type of the individual teeth.

The edge detection engine 186 may implement one or more automated agents configured to find edges or other noteworthy features of the individual tooth segmentation data, or directly from the original 2D images of the dental arch. The edge detection engine 186 may, for example, apply various techniques such as edge detection algorithms to find the edges, tooth lines, and gingiva lines of the individual tooth segmentation data or from the original 2D images of the dental arch.

The 2D extraction datastore 188 may be configured to store data related to the segmentation masks of the upper and lower jaws, individual tooth segmentation data, and edge data, tooth line data, and gingiva line data.

Figure 1E:
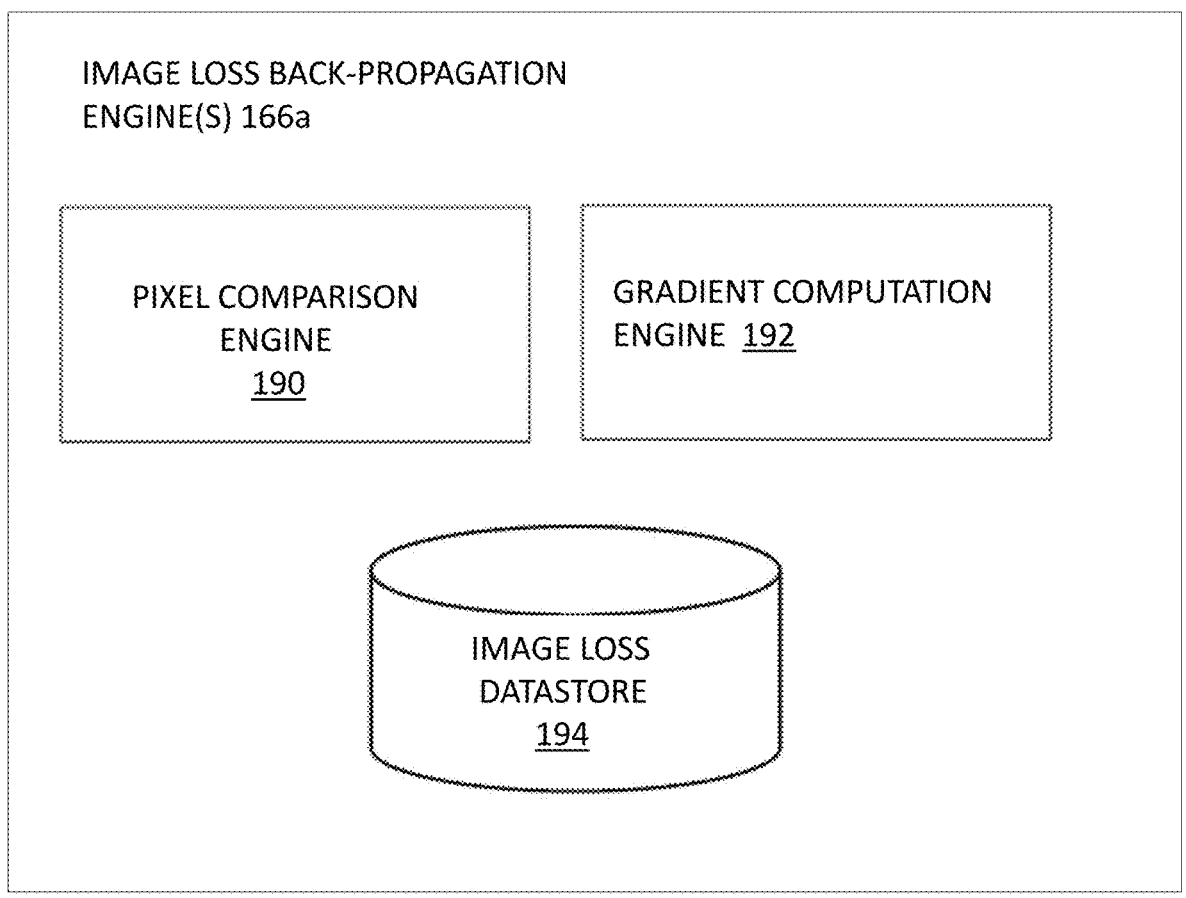
FIG. 1E is a diagram showing an example of an image loss back-propagation engine(s).

FIG. 1E is a diagram showing an example of the image loss back-propagation engine(s) 166a. The image loss back-propagation engine(s) 166a may include a pixel comparison engine 190, a gradient computation engine 192, and an image loss datastore 194. One or more of the modules of the image loss back-propagation engine(s) 166a may be coupled to each other or to modules not shown.

The pixel comparison engine 192 may implement one or more automated agents configured to compare pixel values between the rendered 2D images from the rendering engine 162 and the extracted features from the 2D extraction engine 164 and aggregate the difference at each pixel location into a single image loss function/value.

Since the image loss is a function of all the 3D parameters used by the 3D model engine to form the 3D dental model, the gradient computation engine 192 may implement one or more automated agents configured to compute derivatives/gradients of the image loss with respect to 3D tooth shape parameters, 3D tooth location parameters, 3D tooth orientation parameters, and camera/scanning system parameters. The rendering engine 162 can predict exactly, from the gradient computation engine 192, how the rendered 2D images from the rendering engine will change when varying any of the 3D parameters of the 3D dental model in the 3D model engine. Thus, the gradient computation engine 192 enables gradient back-propagation from the rendered 2D image(s) to 3D tooth geometry parameters (and camera/scanner parameters), allowing for direct parameter optimization. The gradient computation engine 192 can therefore provide updated/optimized 3D parameters to the 3D model engine to improve the accuracy of the 3D dental model.

The image loss datastore 194 may be configured to store data related to the compared pixel values, the image loss at each pixel location, computed derivatives/gradients of the loss with respect to 3D parameters, and updated/optimized 3D parameters.

Figure 1F:
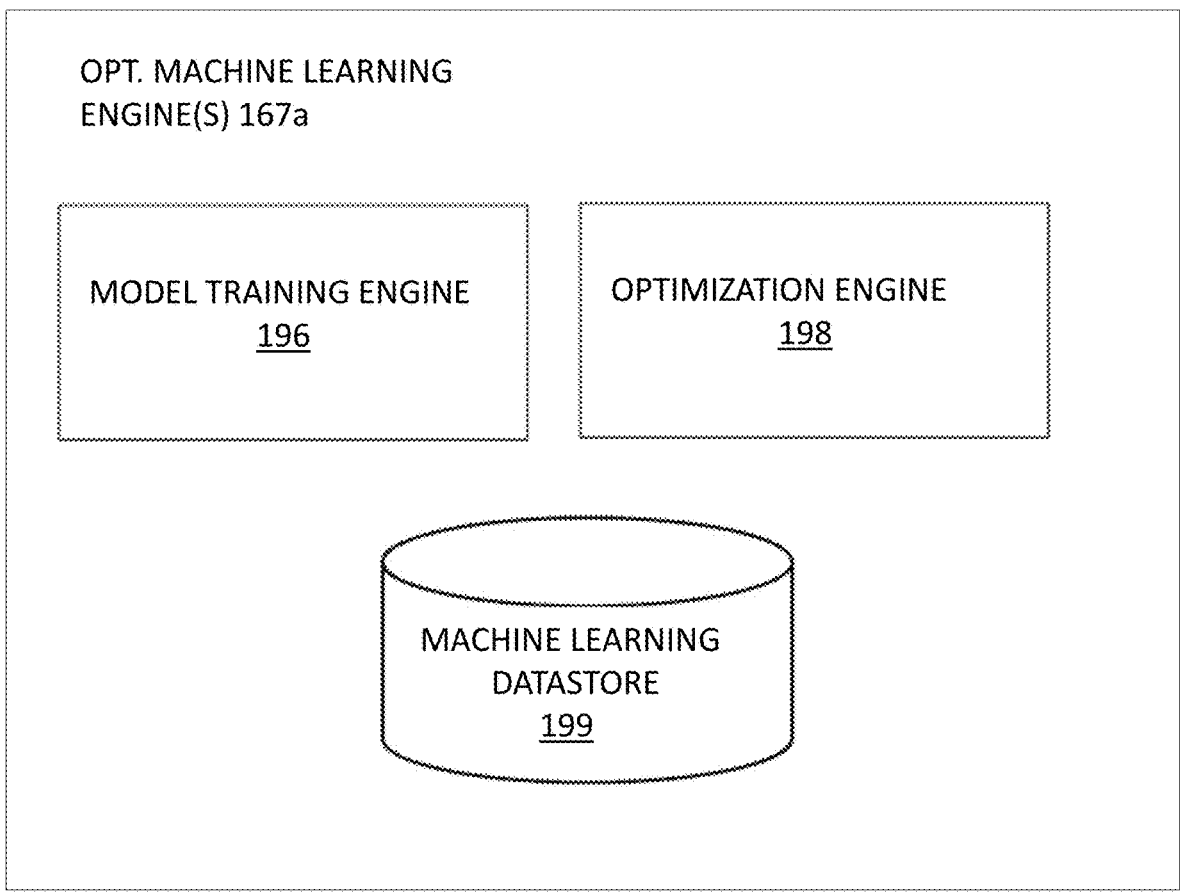
FIG. 1F is a diagram showing an example of a machine learning engine(s).

FIG. 1F is a diagram showing an example of the machine learning engine(s) 167*a*. The machine learning engine(s) 167*a* may include a model training engine 196, an optimization engine 198, and a machine learning datastore 199. One or more of the modules of the machine learning engine(s) 167*a* may be coupled to each other or to modules not shown.

The model training engine 196 may implement one or more automated agents configured to use machine learning techniques to predict 3D dental models from original 2D images of an individual's dentition. In some implementations, the model training engine 196 may train the machine learning model with the extracted features from the 2D original images, the image loss function, and ground truth 3D parameters (and dental models) for patients' dentitions from historical patient data for a certain population. Multiple training cases comprising this information for various patient populations can be used to train the model.

As described above, the ground truth 3D parameters and/or dental models for a certain population can be used to construct a ground truth dataset. A machine learning model can be trained to predict 3D parameters from original 2D images (or processed 2D images as described above). The predicted 3D parameters, can then be used in three successive stages: (1) directly compare predicted 3D parameters with the ground truth 3D parameters; (2) reconstruct 3D dental models from the predicted 3D parameters through the 3D model engine (160), and compare reconstructed 3D dental models with ground truth dental models; (3) render the reconstructed 3D dental model through the differentiable rendering engine (162) to obtain rendered images, and compare with the original 2D images (or processed 2D images) through the image loss engine (166). It should be noted that stages 1-2 above are optional. The comparisons in these three stages are then aggregated into a single loss function to supervise the training process of the machine learning model through a back-propagation optimization process. The machine learning model can be trained with multiple instances of ground truth 3D parameters (or 3D dental models), and original 2D input images (or processed 2D images).

Examples of machine learning systems that may be used by the model training engine include, but are not limited to, Neural Network (primarily Convolutional Neural Networks (CNN)), Decision Tree, Random Forest, Logistic Regression, Support Vector Machine, AdaBoosT, K-Nearest Neighbor (KNN), Quadratic Discriminant Analysis, etc.

The machine learning datastore 199 may be configured to store data related to one or more machine learning models, the compared pixel values, the image loss at each pixel location, computed derivatives/gradients of the loss with respect to 3D parameters, and updated/optimized 3D parameters.

Figure 5:
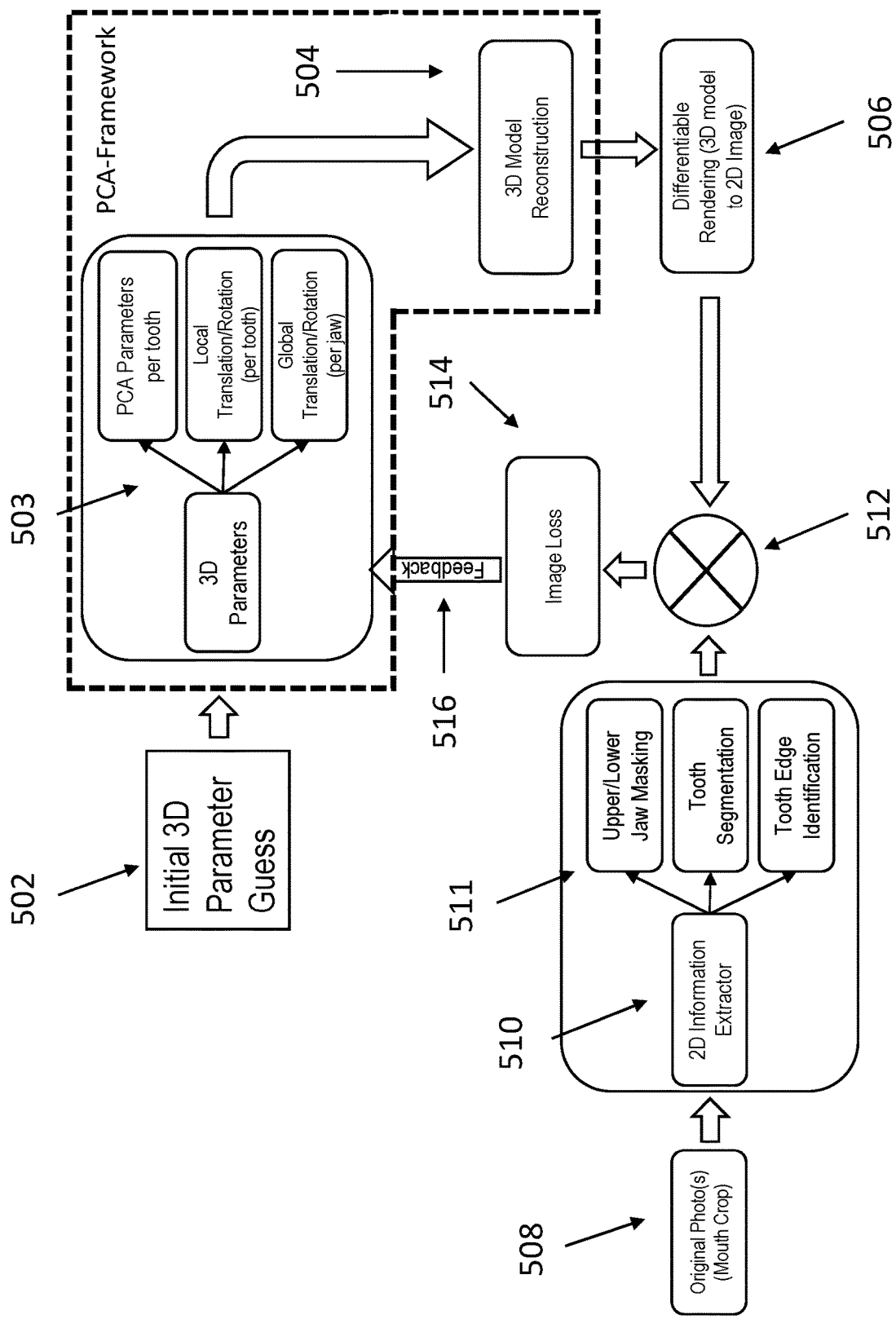
FIG. 5 is a flowchart describing one example of a method of optimizing a 3D model of an individual's teeth.

FIG. 5 illustrates a flowchart of a method for optimizing a 3D dental model of an individual's dentition. This method may be automatically implemented by a system, such as one or more of the systems in the computing environment 100A, shown in FIG. 1A.

At an operation 502, the system may automatically generate or receive initial 3D parameters for construction of an initial 3D dental model. As indicated by arrow 503, the 3D parameters can include 3D tooth shape parameters (e.g., a 3D dental mesh, a 3D point cloud, PCA parameters), camera/scanning system parameters (e.g., focal length, pixel density, contrast, exposure, location and orientation, etc.), 3D tooth location parameters, and 3D tooth orientation parameters (e.g., local translation/rotation for each tooth and global translation/rotation for each jaw of the dentition). The initial set of 3D parameters can be, for example, the average 3D parameters for a 3D dental model from historical patient data. In some implementations, the average 3D parameters can be selected from only historical patient data that represents the individual to be modeled. For example, the mean 3D parameters for similar patients, including patients of similar age, race, gender, etc., can be chosen as the initial set of 3D parameters.

At an operation 504, the system may automatically produce an initial 3D dental model using the initial 3D parameters. The 3D dental model can comprise a 3D dental mesh model, a 3D point cloud, or a PCA representation, etc. In some examples, the 3D dental model can be segmented into individual dental components, such as individual teeth and/or the gingiva.

At an operation 506, the system may automatically use a differentiable renderer to render the 3D model (from operation 504) to one or more rendered 2D images. The rendered 2D image(s) can comprise rendered images of the individual's dentition, or alternatively, of individual teeth or dental features of the individual's dentition from the 3D dental model.

At an operation 508, the system may automatically capture or receive two-dimensional (2D) original photos of an individual's dental arch. The 2D original photos may be generated from a scan collected directly from the individual (e.g., using an intraoral scanner) or indirectly (e.g., by scanning a mold of the individual's dentition, and/or by receiving digital models of the individual's dentition taken by another, etc.

At an operation 510, the system may automatically extract features from the 2D original photos of the individual's dentition. As indicated by arrow 511, the extracted features can include segmentation masks for the upper/lower jaw, individual tooth segmentation and numbering data, tooth edges, tooth lines, and gingiva lines.

At an operation 512, the system may automatically compare pixel values between the rendered 2D images from operation 506 and the extracted features from operation 510. The system may further aggregate the difference at each compared pixel location into a single image loss function.

At an operation 514, the system may automatically compute derivatives/gradients of the image loss from operation 512 with respect to the initial 3D parameters. Thus, the gradient computation enables gradient back-propagation from the image loss of operation 514 to the rendered 2D image(s) of operation 506, and further back to the 3D parameters, allowing for direct parameter optimization. At an operation 516, updated/optimized 3D parameters can be provided to improve the accuracy of the 3D dental model. Operations 503→504→506→512→512→514→516 can be repeated to generate and improve the 3D dental model.

Figure 6:
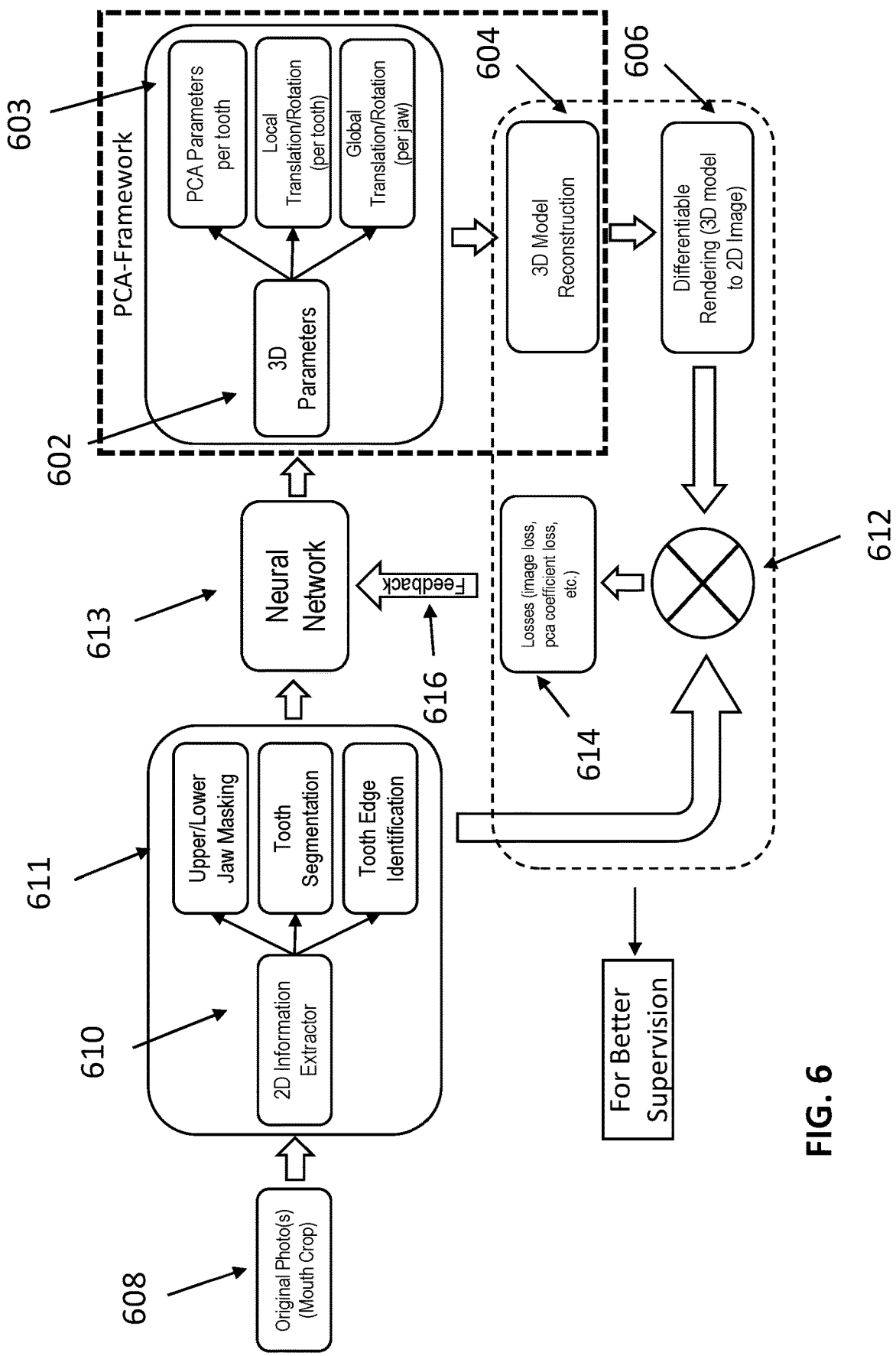
FIG. 6 is a flowchart describing an example of training a machine learning model to predict a 3D model of an individual's teeth.

FIG. 6 illustrates a flowchart of a method for training a machine learning model to predict 3D dental models from original 2D images of an individual's dentition. This method may be automatically implemented by a system, such as one or more of the systems in the computing environment 100A, shown in FIG. 1A.

At an operation 602, the system may automatically receive 3D parameters from the neural network (operation 613). In addition, the operation 602 may also compare received 3D parameters with ground truth parameters, and include the comparison into a loss function in training the neural network model. As indicated by arrow 603, the 3D parameters can include 3D tooth shape parameters (e.g., a 3D dental mesh, a 3D point cloud, PCA parameters), camera/scanning system parameters (e.g., focal length, pixel density, contrast, exposure, location and orientation, etc.), 3D location parameters, and 3D tooth orientation parameters (e.g., local translation/rotation for each tooth and global translation/rotation for each jaw of the dentition).

At an operation 604, the system may automatically produce a 3D dental model using the 3D parameters from operation 602, and compare the reconstructed 3D dental model with the ground truth 3D dental model. The comparison result will be part of a loss function in training the neural network model. The 3D dental model can comprise a 3D dental mesh model, a 3D point cloud, or a PCA representation, etc. In some examples, the 3D dental model can be segmented into individual dental components, such as individual teeth and/or the gingiva.

At an operation 606, the system may automatically use a differentiable renderer to render the 3D model to one or more rendered 2D images. The differentially rendered 2D image(s) can comprise rendered images of the individual's dentition, or alternatively, of individual teeth or dental features of the individual's dentition from the 3D dental model reconstructed from operation 604.

At an operation 608, the system may automatically capture or receive two-dimensional (2D) original photos of an individual's dental arch. The 2D original photos may be generated from a scan collected directly from the individual (e.g., using an intraoral scanner) or indirectly (e.g., by scanning a mold of the individual's dentition, and/or by receiving digital models of the individuals taken by another, etc.

At an operation 610, the system may automatically extract features from the 2D original photos of the individual's dentition. As indicated by arrow 611, the extracted features can include segmentation masks for the upper/lower jaw, individual tooth segmentation data, tooth edges, tooth lines, and gingiva lines. The extracted features can be provided to a neural network 613 (or machine learning model).

At an operation 612, the system may automatically compare pixel values between the rendered 2D images from operation 606 and the extracted features from operation 610. The system may further aggregate the difference at each compared pixel location into a single image loss function.

At an operation 614, the system may automatically aggregate the image loss from operation 612, the 3D parameter difference (between neural network outputs and ground truth parameters, as described in operation 602) and the 3D dental model difference (between reconstructed 3D model and the ground truth 3D dental model, as described in operation 604) into a single modeling loss function. And gradient computation will take place at an operation 616 to back-propagate gradient from the loss function (operation 614) to the rendered 2D image(s) of operation 606 and further back to the 3D parameters of operation 602. At the end of the operation 616, gradient information is fed back to the neural network to improve the neural network training. The operation cycle 613→602→604→606→612→614→616→613 can be repeated to improve the machine learning/neural network accuracy/performance.

Figure 7:
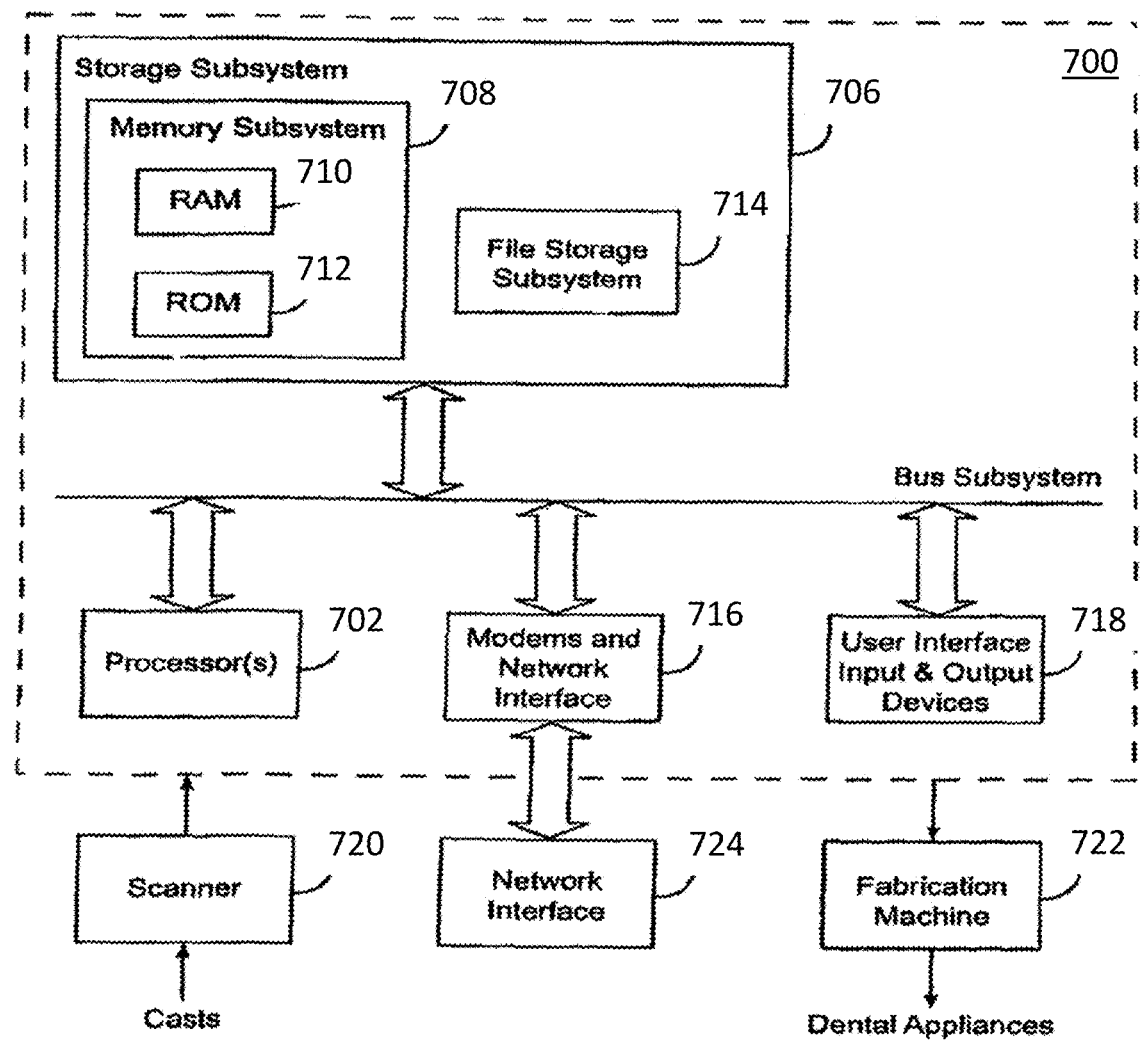
FIG. 7 is a simplified block diagram of a data processing system that may perform the methods described herein.

The methods described herein may be performed by an apparatus, such as a data processing system, which may include hardware, software, and/or firmware for performing many of these steps described above. For example, FIG. 7 is a simplified block diagram of a data processing system 700. Data processing system 700 typically includes at least one processor 702 which communicates with a number of peripheral devices over bus subsystem 704. These peripheral devices typically include a storage subsystem 706 (memory subsystem 708 and file storage subsystem 714), a set of user interface input and output devices 718, and an interface to outside networks 716, including the public switched telephone network. This interface is shown schematically as "Modems and Network Interface" block 716, and is coupled to corresponding interface devices in other data processing systems over communication network interface 724. Data processing system 700 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 706 maintains the basic programming and data constructs that provide the functionality of the present invention. The software modules discussed above are typically stored in storage subsystem 706. Storage subsystem 706 typically comprises memory subsystem 708 and file storage subsystem 714.

Memory subsystem 708 typically includes a number of memories including a main random access memory (RAM) 710 for storage of instructions and data during program execution and a read only memory (ROM) 712 in which fixed instructions are stored. In the case of Macintosh-compatible personal computers the ROM would include portions of the operating system; in the case of IBM-compatible personal computers, this would include the BIOS (basic input/output system).

File storage subsystem 714 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 704 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 720 is responsible for scanning casts of the individual's teeth obtained either from the individual or from an orthodontist and providing the scanned digital data set information to data processing system 700 for further processing. In a distributed environment, scanner 720 may be located at a remote location and communicate scanned digital data set information to data processing system 700 over network interface 724.

Fabrication machine 722 fabricates dental appliances based on intermediate and final data set information acquired from data processing system 700. In a distributed environment, fabrication machine 722 may be located at a remote location and acquire data set information from data processing system 700 over network interface 724.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Thus, any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and/or methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the individual matter may be practiced. As mentioned, other embodiments may be utilized and derived there from, such that structural and logical substitutions and changes may be made without departing from the scope of this disclosure. Such embodiments of the inventive patient matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of forming a three-dimensional (3D) model of an individual's dentition, the method comprising:
    obtaining one or more two-dimensional (2D) original images depicting at least a portion of the individual's dentition;
    extracting features from the one or more 2D original images;
    providing the extracted features to a trained neural network that is trained to construct a parametric 3D dental model using the extracted features and a set of network weights, wherein the network weights are based on results from a loss function comparing a plurality of 2D original images of historical patient dentitions with corresponding one or more 2D differentiable renderings generated based on 3D parameters associated with the patient dentitions; and
    outputting, from the trained neural network, the parametric 3D dental model of the individual's dentition.

2. The method of claim 1, wherein the network weights are based on gradients of loss determined from the results from the loss function.

3. The method of claim 1, wherein results of the loss function are derived from a pixel by pixel comparison between the plurality of 2D original images of the historical patient dentitions and the corresponding one or more 2D differential renderings.

4. The method of claim 1, wherein the 3D parameters for a particular dentition of the historical patient dentitions comprise one or more of: a local translation for each of a plurality of teeth of the particular patient dentition, a local rotation for each of a plurality of teeth of the particular patient dentition, a global translation for a jaw of the particular patient dentition, and a global rotation for a jaw of the particular patient dentition.

5. The method of claim 1, wherein extracting features from the one or more 2D original images comprises extracting one or more of: a tooth mask for an upper jaw or a lower jaw; tooth segmentation data; tooth numbering data; and dental edge information.

6. The method of claim 1, further comprising comparing the parametric 3D dental model to an orthodontic treatment plan of the individual and determining whether the individual's dentition is tracking the orthodontic treatment plan.

7. The method of claim 6, further comprising modifying the orthodontic treatment plan based on the comparison between the parametric 3D dental model and the orthodontic treatment plan.

8. A system for forming a three-dimensional (3D) dental model of an individual's dentition, the system comprising:
one or more processors; and
a memory coupled to the one or more processors, the memory storing computer-program instructions, that, when executed by the one or more processors, perform a computer-implemented method comprising:
obtaining one or more two-dimensional (2D) original images depicting at least a portion of the individual's dentition;
extracting features from the one or more 2D original images;
providing the extracted features to a trained neural network that is trained to construct a parametric 3D dental model using the extracted features and a set of network weights, wherein the network weights are based on results from a loss function comparing a plurality of 2D original images of historical patient dentitions with corresponding one or more 2D differentiable renderings generated based on 3D parameters associated with the patient dentitions; and
outputting, from the trained neural network, the parametric 3D dental model of the individual's dentition.

9. The system of claim 8, wherein the network weights are based on gradients of loss determined from the results from the loss function.

10. The system of claim 8, wherein results of the loss function are derived from a pixel by pixel comparison between the plurality of 2D original images of the historical patient dentitions and the corresponding one or more 2D differential renderings.

11. The system of claim 8, wherein the 3D parameters for a particular dentition of the historical patient dentitions comprise one or more of: a local translation for each of a plurality of teeth of the particular patient dentition, a local rotation for each of a plurality of teeth of the particular patient dentition, a global translation for a jaw of the particular patient dentition, and a global rotation for a jaw of the particular patient dentition.

12. The system of claim 8, wherein extracting features from the one or more 2D original images comprises extracting one or more of: a tooth mask for an upper jaw or a lower jaw; tooth segmentation data; tooth numbering data; and dental edge information.

13. The system of claim 8, further comprising comparing the parametric 3D dental model to an orthodontic treatment plan of the individual and determining whether the individual's dentition is tracking the orthodontic treatment plan.

14. The system of claim 13, further comprising modifying the orthodontic treatment plan based on the comparison between the parametric 3D dental model and the orthodontic treatment plan.

15. A non-transitory, computer-readable medium including contents that are configured to cause one or more processors to perform a method comprising:
obtaining one or more two-dimensional (2D) original images depicting at least a portion of the individual's dentition;
extracting features from the one or more 2D original images;
providing the extracted features to a trained neural network that is trained to construct a parametric 3D dental model using the extracted features and a set of network weights, wherein the network weights are based on results from a loss function comparing a plurality of 2D original images of historical patient dentitions with corresponding one or more 2D differentiable renderings generated based on 3D parameters associated with the patient dentitions; and
outputting, from the trained neural network, the parametric 3D dental model of the individual's dentition.

16. The non-transitory, computer-readable medium of claim 15, wherein the network weights are based on gradients of loss determined from the results from the loss function.

17. The non-transitory, computer-readable medium of claim 15, wherein results of the loss function are derived from a pixel by pixel comparison between the plurality of 2D original images of the historical patient dentitions and the corresponding one or more 2D differential renderings.

18. The non-transitory, computer-readable medium of claim 15, wherein the 3D parameters for a particular dentition of the historical patient dentitions comprise one or more of: a local translation for each of a plurality of teeth of the particular patient dentition, a local rotation for each of a plurality of teeth of the particular patient dentition, a global translation for a jaw of the particular patient dentition, and a global rotation for a jaw of the particular patient dentition.

19. The non-transitory, computer-readable medium of claim 15, wherein extracting features from the one or more 2D original images comprises extracting one or more of: a tooth mask for an upper jaw or a lower jaw; tooth segmentation data; tooth numbering data; and dental edge information.

20. The non-transitory, computer-readable medium of claim 15, further comprising comparing the parametric 3D dental model to an orthodontic treatment plan of the individual and determining whether the individual's dentition is tracking the orthodontic treatment plan.

21. The non-transitory, computer-readable medium of claim 20, further comprising modifying the orthodontic treatment plan based on the comparison between the parametric 3D dental model and the orthodontic treatment plan.

* * * * *